(12) United States Patent
Castaneda

(10) Patent No.: US 11,071,680 B2
(45) Date of Patent: Jul. 27, 2021

(54) ERECTILE DYSFUNCTION TREATMENT SYSTEM AND METHOD

(71) Applicant: Sergio Castaneda, Las Vegas, NV (US)

(72) Inventor: Sergio Castaneda, Las Vegas, NV (US)

( * ) Notice: Subject to any disclaimer, the term of this patent is extended or adjusted under 35 U.S.C. 154(b) by 234 days.

(21) Appl. No.: 16/355,248

(22) Filed: Mar. 15, 2019

(65) Prior Publication Data
US 2020/0289362 A1 Sep. 17, 2020

(51) Int. Cl.
*A61H 19/00* (2006.01)
*A61H 9/00* (2006.01)
*A61F 5/41* (2006.01)

(52) U.S. Cl.
CPC ............... *A61H 19/32* (2013.01); *A61F 5/41* (2013.01); *A61H 9/0057* (2013.01); *A61H 9/0071* (2013.01); *A61F 2005/411* (2013.01); *A61F 2005/412* (2013.01)

(58) Field of Classification Search
CPC ........ A61H 19/00; A61H 19/30; A61H 19/32; A61H 9/0057; A61F 5/41; A61F 2005/411; A61F 2005/412
See application file for complete search history.

(56) References Cited

U.S. PATENT DOCUMENTS

| | | | | |
|---|---|---|---|---|
| 8,900,121 B2* | 12/2014 | Moon | ........................ | A61F 5/41 600/39 |
| 2005/0124854 A1* | 6/2005 | Suchy | .................. | A61H 1/0218 600/39 |
| 2007/0093687 A1* | 4/2007 | Hoefer | ....................... | A61F 5/41 600/41 |
| 2007/0179337 A1* | 8/2007 | Kalvatanond | ............. | A61F 5/41 600/38 |
| 2009/0024063 A1* | 1/2009 | Kalvatanond | ........ | A61N 5/0613 601/15 |
| 2011/0172489 A1* | 7/2011 | Muller | ....................... | A61F 5/41 600/39 |
| 2018/0228690 A1* | 8/2018 | Hirsch | ................... | A61H 19/32 |

* cited by examiner

*Primary Examiner* — John P Lacyk
(74) *Attorney, Agent, or Firm* — The Thornton Firm, LLC

(57) ABSTRACT

An erectile dysfunction treatment system comprising a base unit capable of interfacing with the human body, a frame unit, a vacuum cylinder unit, a cap assembly with distraction means, a yoke assembly capable of interfacing with a human penis, and at least one vacuum line attachment. Use of the system involves the user preparing and inserting the penis into the yoke assembly, securing the penis in the yoke assembly, securing the frame around the penis secured in the yoke assembly, moving the yoke assembly so as to apply a distractive force to the inserted and secured penis, applying a vacuum to the inserted and secured penis and allowing distractive force and vacuum to operate for a therapeutic amount of time. The erectile dysfunction treatment system may be used to treat disorders such as Peyronie's disease and other forms of erectile dysfunction and may be used to enhance penile length and girth.

18 Claims, 16 Drawing Sheets

ERECTILE DYSFUNCTION TREATMENT SYSTEM AND METHOD

CROSS-REFERENCE TO RELATED APPLICATIONS

Not applicable

RELATED CO-PENDING U.S. PATENT APPLICATIONS

Not applicable.

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office, patent file or records, but otherwise reserves all copyright rights whatsoever.

BACKGROUND OF THE INVENTION

1. Field of the Invention

One or more embodiments of the invention generally relate to erectile dysfunction treatment systems. More particularly, embodiments of the invention relate to an improved erectile dysfunction treatment system and method of use that involves the use of both vacuum and distraction techniques to straighten, increase blood flow to, and add both length and girth to the penis.

2. Description of the Related Art

Male erectile dysfunction is a common medical problem. It has many roots both physiological and psychological, but its effects may be devastating for both the individual and the individual's partner. Erectile dysfunction and/or penile shortening may be the result of various causes such as common aging or surgical procedures such as radical prostatectomy and transurethral resection of the prostate.

Closely related to erectile dysfunction, Peyronie's disease (PD) is a connective tissue disorder involving the tunica albuginea layer of the penis. The fibrotic process that occurs may result in the formation of plaque, one of the classic findings on physical examination of the patient. Patients afflicted by this disorder may present with pain, deformity (such as penile curvature or penile shortening) and/or erectile dysfunction (ED).

Among the more extreme methods of erectile dysfunction and Peyronie's disease involve surgical procedures. Some procedures involve removal of fibrotic tissue. Other treatments involve the addition of implants. One common treatment is the use of relatively stiff flexible rods surgically implanted in the penis. Another method is the implantation of slim tubular balloons in the penis rather than rods which may be inflated with fluid from a reservoir when an erection is desired. Though proven effective, these methods of treatment come with serious risks which deter numerous men from seeking such treatment. And while surgical therapy has proven itself to be a definitive treatment for penile curvature associated with Peyronie's disease, less invasive options are currently a desired alternative.

Several less risky methods of treatment for erectile dysfunction and Peyronie's disease are now in use ranging from drug therapy to the use of medical devices. In addition to erectile dysfunction treatment, many males wish to enhance their penis size and sexual performance, to which analogous treatments are available. The use of medical devices is an attractive alternative to surgery in the interest of avoiding invasive and risky procedures. Moreover, medical devices work to treat multiple aspects of erectile dysfunction and Peyronie's disease, and to intervene before the effects of Peyronie's disease may no longer be reversible.

Among the more conventional medical treatment devices commonly used, vacuum enlargement pumps have been known in the art for many years. The manner in which such pumps work is by placing a chamber over a flaccid penis and evacuating the chamber. The evacuation causes a pressure differential between the inside and outside of the chamber. This reduced pressure induces the penis to fill with blood and become erect. Erections may be maintained through the use of constriction bands which prevents blood from leaving the engorged and erect penis.

Most vacuum enlargement pump systems commonly known in the art comprise a chamber having a diaphragm at a lower end thereof and a tube attached at an upper end thereof. The tube is connected to a hand-held vacuum pump device which is usually in the form of an inflatable bulb or a trigger-style having a non-return valve therein. In use, a user places the penis through the diaphragm into the chamber and removes air from the chamber by use of the pump.

Penile traction devices are another medical device for treating erectile dysfunction and for increasing penile length. These devices usually consist of a plastic support ring, a silicone band, and two dynamic rods. Penile traction therapy works by holding the penis in a cradle and subjecting it to gentle and progressive traction forces that can be achieved by the addition of small metal extensions to the dynamic rods and cradle frame every few weeks. As the penile tissues are slowly yet surely stretched, which causes microscopic tears which, in theory, the body heals by producing cells to repair the gap. With each repair phase, the penile tissues expand. The desired end result being that the penis lengthens and widens and produces firmer and longer-lasting erections.

Both penile vacuum enlargement pumps and penile traction devices have limitations though. Most notably, enlargement pumps and traction devices are currently used separately and independent from one another. Presently, there exists a need for a more versatile male erectile dysfunction treatment system and method which combines the benefits of vacuum enlargement pump therapy with penile traction therapy through the use of a single device.

SUMMARY

The present invention introduces a new technology, which fulfils the need for a more versatile male erectile dysfunction treatment system and method which combines the benefits of vacuum enlargement pump therapy with penile traction therapy through the use of a single device. The erectile dysfunction treatment system comprises a base unit capable of interfacing with the human body, a frame unit, a vacuum cylinder assembly, a cap assembly, a yoke assembly capable of interfacing with a human penis, a distraction means; and at least one vacuum line attachment. The erectile dysfunction treatment system and method is versatile and readily implementable to treat a wide variety of erectile dysfunction problems and may serve to enhance penis length and girth.

In embodiments of the present invention, a pump assembly may be detachably affixed to the vacuum cylinder unit in more than one way, so that when detached and connected with a length of tubing, the pump assembly may be easily worked with the erectile dysfunction treatment system in place. The present invention is intended to be used with numerous pumps known and available on the market. This feature provides two operational attributes in one device, both a vacuum device and a traction device.

Use of the erectile dysfunction treatment system involves the user preparing and inserting the penis into the yoke assembly, securing the penis in the yoke assembly, securing the frame around the penis secured in the yoke assembly, moving the yoke assembly so as to apply a distractive force to the inserted and secured penis, applying a vacuum to the inserted and secured penis and allowing distractive force and vacuum to operate for a therapeutic amount of time.

The exemplary dysfunction treatment system may be prescribed and/or sold as a single unit or as a kit with interchangeable components. For example, differing base units may be made for differing users with differing needs. In other embodiments, differing cap assemblies with differing distraction means may be sold. In yet other embodiments, vacuum tube assemblies may be sold in lieu of frame seal attachments. A primary object of the erectile dysfunction treatment system is to provide a patient the widest variety of treatment options in a customizable medical device.

BRIEF DESCRIPTION OF THE DRAWINGS

The invention directed by way of example, and not by way of limitation, in the figures of the accompanying drawings and in which like reference numerals refer to similar elements and in which.

Figure 1:
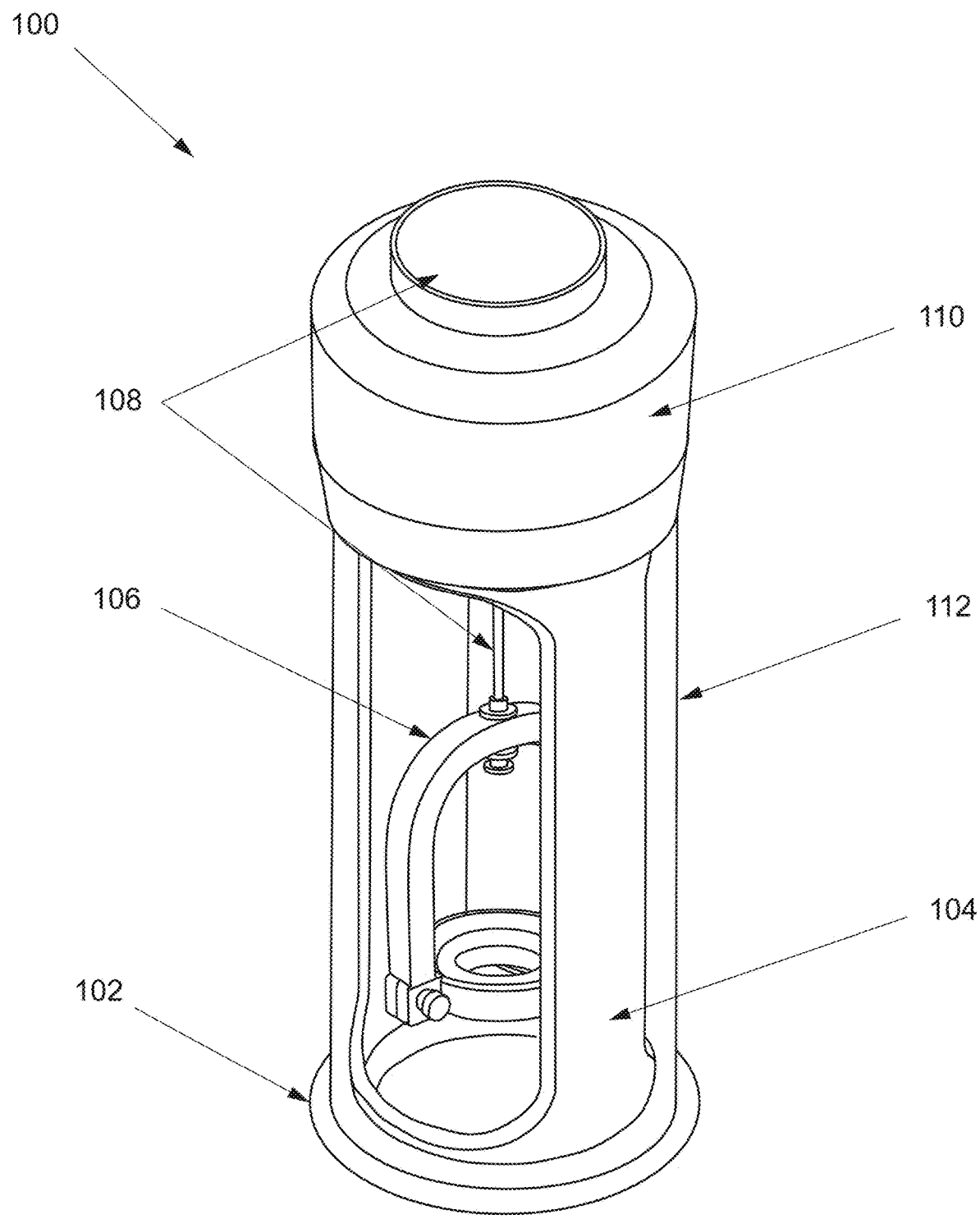
FIG. 1 is a perspective view of the exemplary erectile dysfunction treatment system in accordance with an embodiment of the invention.

Unless otherwise indicated illustrations in the figures are not necessarily drawn to scale.

DETAILED DESCRIPTION OF THE PREFERRED EMBODIMENTS

Terminology used herein is used for the purpose of describing particular embodiments only, and is not intended to limit the scope of the present invention. It must be understood that as used herein and in the appended claims, the singular forms "a," "an," and "the" include the plural reference unless the context clearly dictates otherwise. For example, a reference to "an element" is a reference to one or more elements and includes all equivalents known to those skilled in the art. All conjunctions used are to be understood in the most inclusive sense possible. Thus, the word "or" should be understood as having the definition of a logical "or" rather than that of a logical "exclusive or" unless the context clearly necessitates otherwise. Language that may be construed to express approximation should be so understood unless the context clearly dictates otherwise.

Unless defined otherwise, all technical and scientific terms used herein have the same meanings as commonly understood by a person of ordinary skill in the art to which this invention belongs. Preferred methods, techniques, devices, and materials are described. But any methods, techniques, devices, or materials similar or equivalent to those described herein may be used in the practice or testing of the present invention. Structures described herein should also be understood to refer to functional equivalents of such structures.

References to "one embodiment," "an embodiment," "various embodiments," etc., may indicate that the embodiment(s) of the invention so described may include particular features, structures, or characteristics. However, not every embodiment necessarily includes the particular features, structures, or characteristics. Further, repeated use of the phrase "in one embodiment," or "in an exemplary embodiment," do not necessarily refer to the same embodiment although they may. A description of an embodiment with several components in communication with each other does not imply that all such components are required. On the contrary, a variety of optional components are described to illustrate the wide variety of possible embodiments of the present invention.

As is well known to those skilled in the art, many careful considerations and compromises typically must be made when designing for the optimal manufacture of a commercial implementation of such an erectile dysfunction treatment system. A commercial implementation in accordance with the spirit and teachings of the invention may be configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art.

The exemplary male erectile dysfunction treatment system and method will now be described in detail with reference to embodiments thereof as illustrated in the accompanying drawings.

FIG. 1 is a perspective view of the exemplary erectile dysfunction treatment system in accordance with an embodiment of the invention. In embodiments of the invention, the exemplary erectile dysfunction treatment system 100 comprises a base unit 102, a frame 104, a yoke unit 106, a distraction means 108, a cap assembly 110, and a vacuum cylinder unit 112. In embodiments of the invention, the individual components may be assembled to form a single apparatus.

Figure 2:
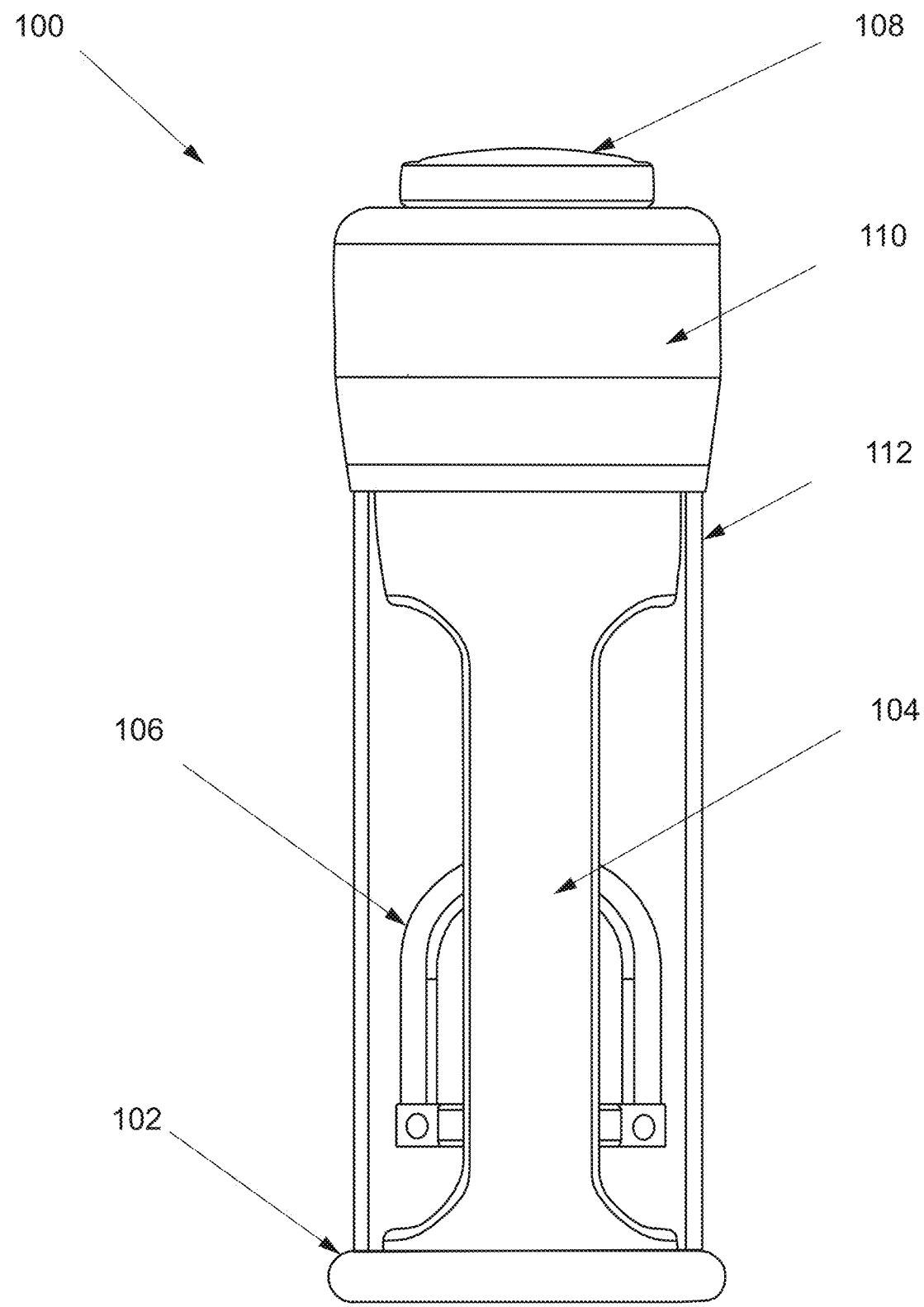
FIG. 2 is a side view of the exemplary erectile dysfunction treatment system in accordance with an embodiment of the invention.

FIG. 2 is a side view of the exemplary erectile dysfunction treatment system in accordance with an embodiment of the invention. In embodiments of the invention, the exemplary erectile dysfunction treatment system 100 comprises a base unit 102, a frame 104, a yoke unit 106, a distraction means 108, a cap assembly 110, and a vacuum cylinder unit 112. In various embodiments of the invention the cap assembly attaches to the frame. The base unit 102 also attaches to the frame 104. A vacuum cylinder unit 112 may slide over the frame 104 to rest on the base unit 102 and the cap assembly 110 then may slide over the vacuum cylinder to attach to the frame. The vacuum cylinder unit 112 is held in place by gaskets located in the cap assembly and the base unit. When a vacuum is applied to the vacuum cylinder unit 112, the exemplary erectile dysfunction treatment system is sealed in such a manner so as to hold the components together and to maintain a vacuum for a therapeutic amount of time.

Figure 3:
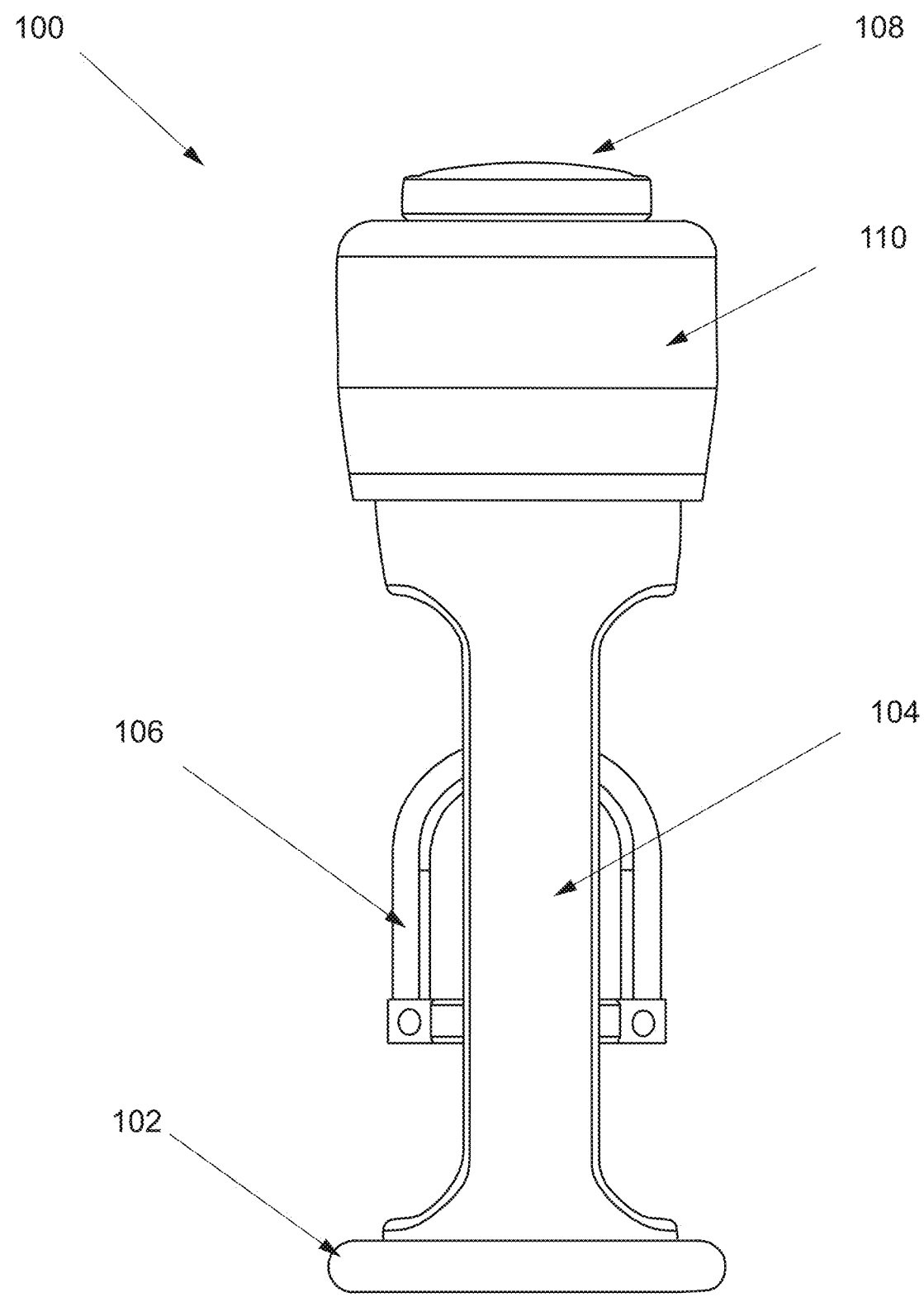
FIG. 3 is a side view of the exemplary erectile dysfunction treatment system in accordance with an alternative embodiment of the invention.

FIG. 3 is a side view of the exemplary erectile dysfunction treatment system in accordance with an alternative embodiment of the invention. In one embodiment of the invention, the exemplary erectile dysfunction treatment system 100 comprises a base unit 102, a frame 104, a yoke unit 106, a distraction means 108, and a cap assembly 110. In such an embodiment, the exemplary erectile dysfunction treatment system may be used without a vacuum cylinder for distraction therapy alone. The cap assembly and base unit attach to the frame irrespective of whether the vacuum cylinder unit is used.

Figure 4:
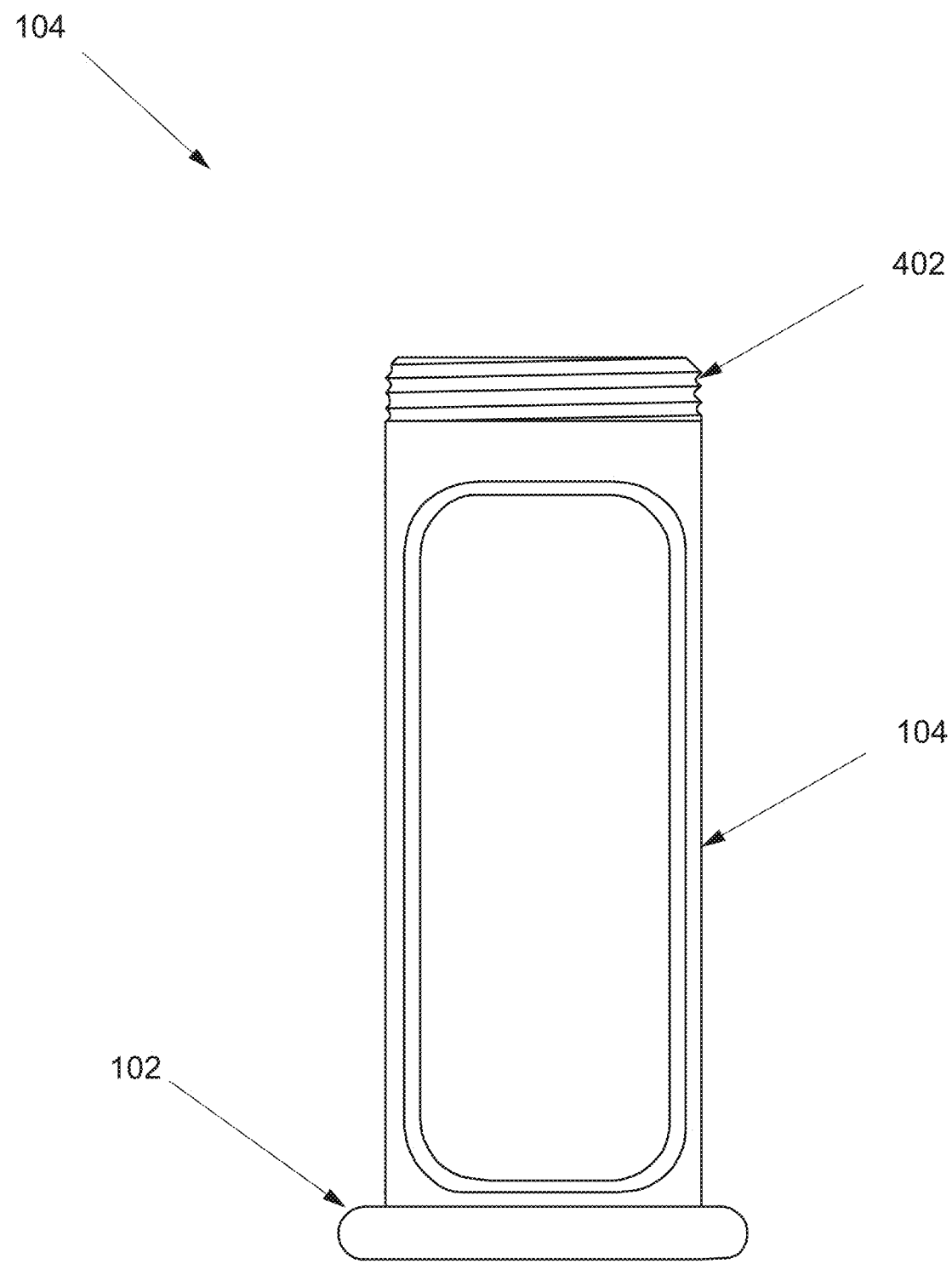
FIG. 4 is a side view of the frame unit of the exemplary erectile dysfunction treatment system in accordance with an embodiment of the invention.

FIG. 4 is a side view of the frame unit of the exemplary erectile dysfunction treatment system in accordance with an embodiment of the invention. In the preferred embodiment of the invention, the frame is cylindrically shaped with two open sides. In embodiments of the invention, the frame unit may be made from a medical-grade polycarbonate resin plastic. However, persons skilled in the art will readily appreciate that alternative embodiments may be made from a number of materials such as, but not limited to, metal and metal alloys, clear acrylic plastics, ABS plastic, polycarbonates, polyvinyl chloride (PVC), or various other plastic equivalents. In this view, the frame unit 104 is a cylinder with two openings for a user to access the yoke unit and distraction means as well as to make adjustments to the contents thereof. In various embodiments of the invention, the cap end of the frame unit 402 may be threaded so as to attach to the cap assembly. In other embodiments, the cap end of the frame unit 402 may utilize a different attachment means such as, but not limited to, a bayonet mount or other attachment means known and understood in the art. Persons skilled in the art will understand that a vacuum seal may be formed when the frame attaches to the cap assembly.

Figure 5:
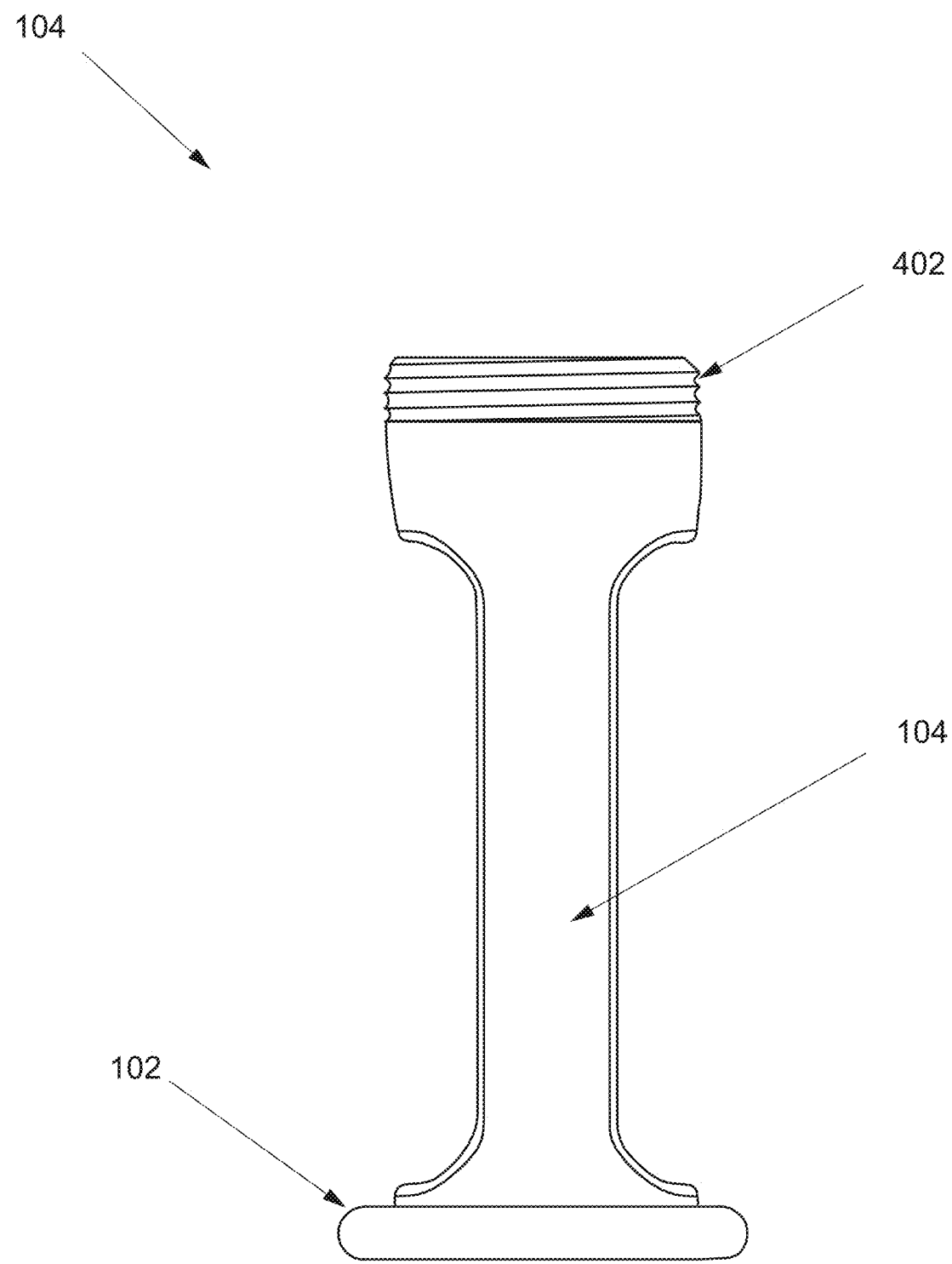
FIG. 5 is a side view of the frame unit of the exemplary erectile dysfunction treatment system in accordance with an embodiment of the invention.

FIG. 5 is a side view of the frame unit of the exemplary erectile dysfunction treatment system in accordance with an embodiment of the invention. In the preferred embodiment of the invention, the frame is cylindrically shaped with two open sides. In the embodiments of the invention, the frame unit may be made from a medical-grade polycarbonate resin plastic. However, persons skilled in the art will readily appreciate that alternative embodiments may be made from a number of materials such as, but not limited to, metal and metal alloys, clear acrylic plastics, ABS plastic, polycarbonates, polyvinyl chloride (PVC), or various other plastic equivalents. In this view, the frame 104 is a cylinder with two openings for a user to access the yoke unit and distraction means as well as to make adjustments to the contents thereof. In various embodiments of the invention, the cap end of the frame unit 402 may be threaded so as to attach to the cap assembly. In other embodiments, the cap end of the frame unit 402 may utilize a different attachment means such as, but not limited to, a bayonet mount or other attachment means known and understood in the art. Persons skilled in the art will understand that a vacuum seal may be formed when the frame attaches to the cap assembly.

Figure 6:
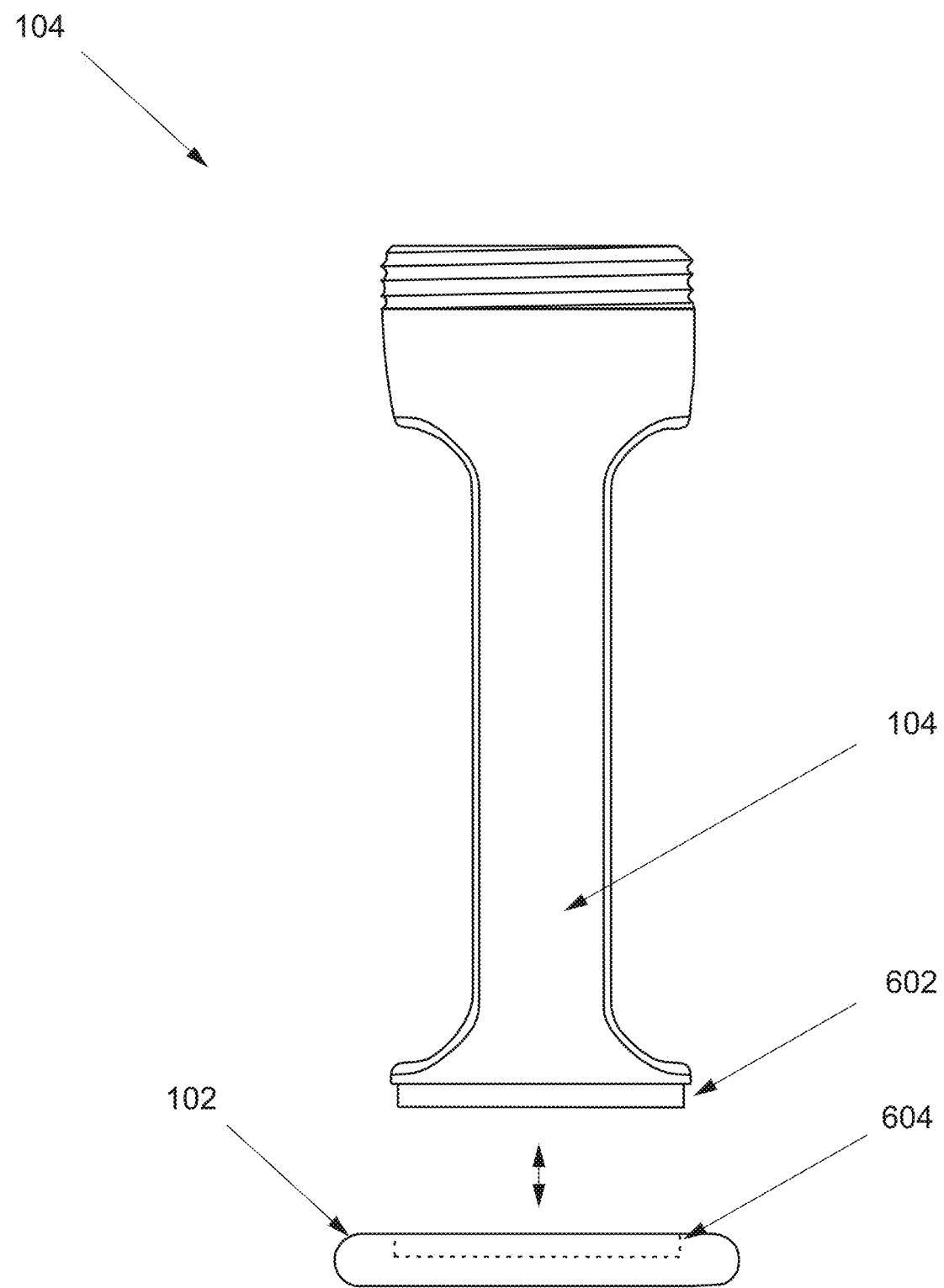
FIG. 6 is a side exploded view of the frame unit and base unit of the exemplary erectile dysfunction treatment system in accordance with an embodiment of the invention.

FIG. 6 is a side exploded view of the frame unit and base unit of the exemplary erectile dysfunction treatment system in accordance with an embodiment of the invention. In embodiments of the invention, the base unit serves to interface with the pubic are of a human body. The base unit 102 is, in general, circular shaped and is attachable to the frame 104. The base end of the frame 602 may be shaped in such a way so as to slide into the base unit 102. The base unit may be made from materials which may interface with the pubic area of a human male as well as form an airtight gasket when the vacuum cylinder unit is used and vacuum is applied to the vacuum cylinder. In the preferred embodiment of the invention, the base may be made from molded silicone, but other suitable materials such as, but not limited to, rubber, latex foam or various plastics. In embodiments of the invention, the base unit may assume differing shapes and forms for differing users and may be sold as attachable and interchangeable accessories. Persons skilled in the art will readily appreciate that there are numerous ways to attach such a base unit to a frame such as, but not limited to, simple frictional attachment, threaded ends or a bayonet mounting mechanism. In the preferred embodiment, the base unit 102 has an attachment point 604 specifically configured to attach to the frame 102, and simply slides over the end of the base end of the frame 602.

Figure 7A:
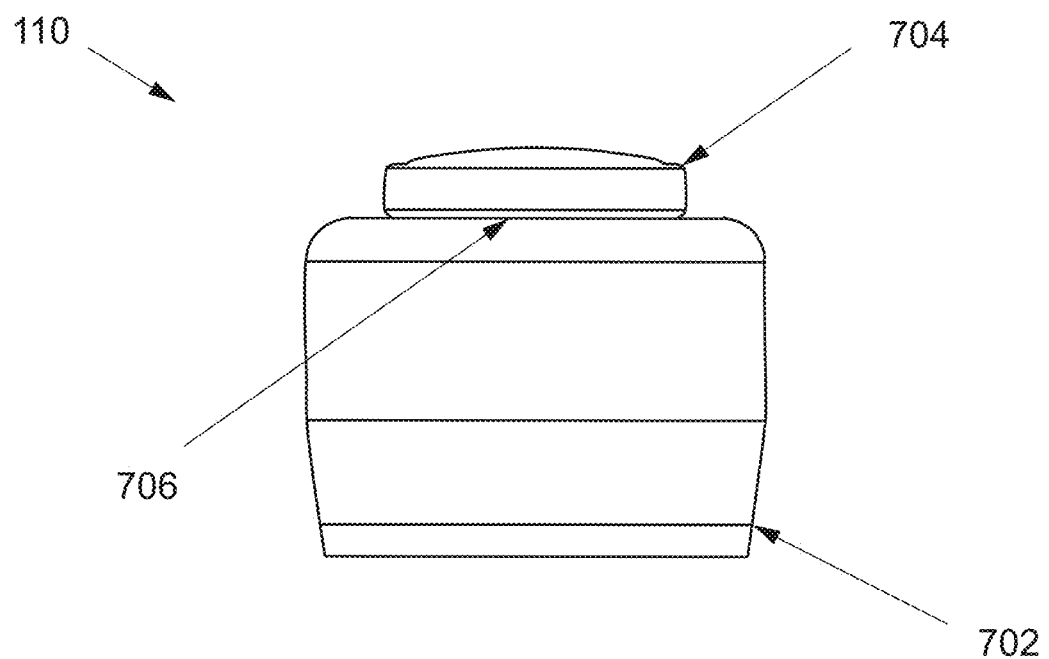
FIG. 7A is a side view of the cap assembly of the exemplary erectile dysfunction treatment system in accordance with an embodiment of the invention.

FIG. 7A is a side view of the cap assembly of the exemplary erectile dysfunction treatment system in accordance with an embodiment of the invention. In various embodiments of the invention, the cap assembly 110 consists of a female end 702 which couples with the frame unit and vacuum cylinder unit. A hand dial or crank 704 for moving the distraction means and the yoke assembly is located on the top of the cap assembly 110. Persons skilled in the art will readily appreciate that numerous hand dials or cranks may be used to move the distraction means and yoke assembly depending on the type of distraction means used. For example, and not by way of limitation, a common star nut may attach to a bolt for a distraction means for moving the yoke assembly.

Figure 7B:
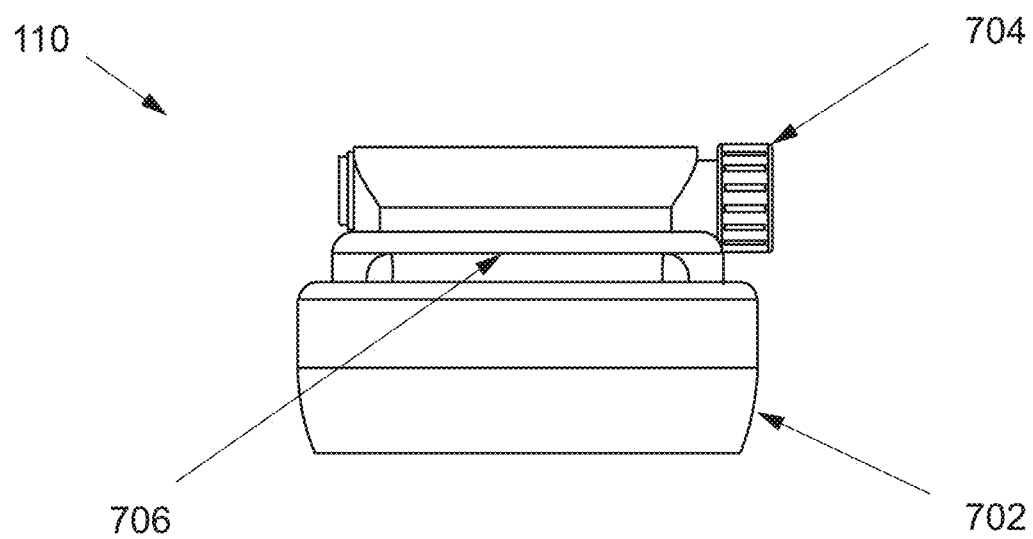
FIG. 7B is a side view of the view of the cap assembly of the exemplary erectile dysfunction treatment system in accordance with an alternative embodiment of the invention.

FIG. 7B is a side view of the view of the cap assembly of the exemplary erectile dysfunction treatment system in accordance with an alternative embodiment of the invention. In various embodiments of the invention, the cap assembly 110 consists of a female end 702 which couples with the frame unit and vacuum cylinder unit. A hand dial or crank 704 for moving the distraction means is located on the top of the cap assembly 110. Persons skilled in the art will readily appreciate that numerous hand dials or cranks may be used to move the distraction means and yoke assembly depending on the type of distraction means used. For example, and not by way of limitation, a ratcheting spool with a cable as a distraction means for moving the yoke assembly.

The two illustrations of the cap assembly with distraction means are not meant to be limiting. It will become readily apparent to persons skilled in the art that numerous distraction means may be used with the cap assembly such as, but not limited to, alternative spooling mechanisms which run both parallel and perpendicular to the cap assembly. In one embodiment, an electric motor may be used to turn the screw mechanism or spool and cable mechanism. In another embodiment, a ratchet rod and gear and pawl means may be used with one or more rods. In another embodiment, a smooth rod and soft pawl ratcheting means may be used with one or more rods. In another embodiment, a vacuum pump may be used as a distraction means.

Figure 8A:
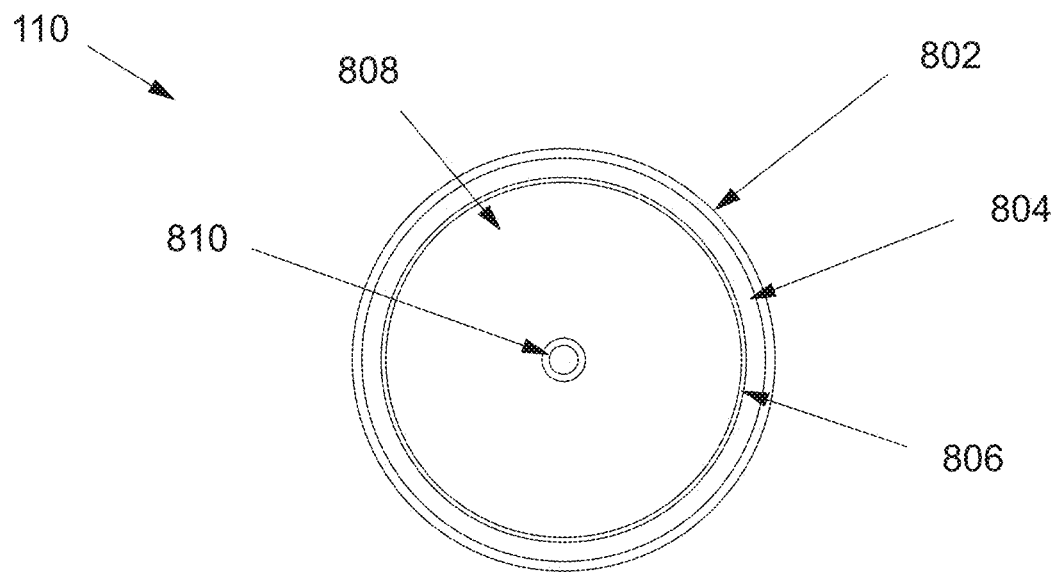
FIG. 8A is a bottom view of the cap assembly of the exemplary erectile dysfunction treatment system in accordance with an embodiment of the invention.

FIG. 8A is a bottom view of the cap assembly of the exemplary erectile dysfunction treatment system in accordance with an embodiment of the invention. In an embodiment of the present invention, the cap assembly consists of an outer shell 802, a gasket 804, a threaded attachment means 806, a cap or lid 808 and an opening 810 for the distraction means. Persons skilled in the art will understand that the opening 810 for the distraction means may include a gasket or other sealing mechanism so as to create a seal. In embodiments of the invention, the outer shell 802 of the cap assembly may be made from a medical-grade polycarbonate resin plastic. However, persons skilled in the art will readily appreciate that alternative embodiments may be made from a number of materials such as, but not limited to, metal and metal alloys, clear acrylic plastics, ABS plastic, HDPE, polycarbonates, polyvinyl chloride (PVC), or various other plastic equivalents. A cap or lid 808 may be a simple extension of the outer shell to form a single unit. In embodiments of the invention, the gasket 804 may be made from materials such as, but not limited to, molded silicone, rubber, latex foam, cork, or various plastics capable of creating an airtight seal for the vacuum cylinder unit. In embodiments of the invention, the threaded attachment means 806 is a female threaded attachment point where the cap end of the frame unit may be inserted and attached. Persons skilled in the art will readily appreciate that such an attachment may be accomplished through numerous means such as, but not limited to, a threaded screw mechanism or a bayonet mount mechanism. The cap assembly may be molded in such a manner that such attachment means may be part of the cap assembly itself.

Figure 8B:
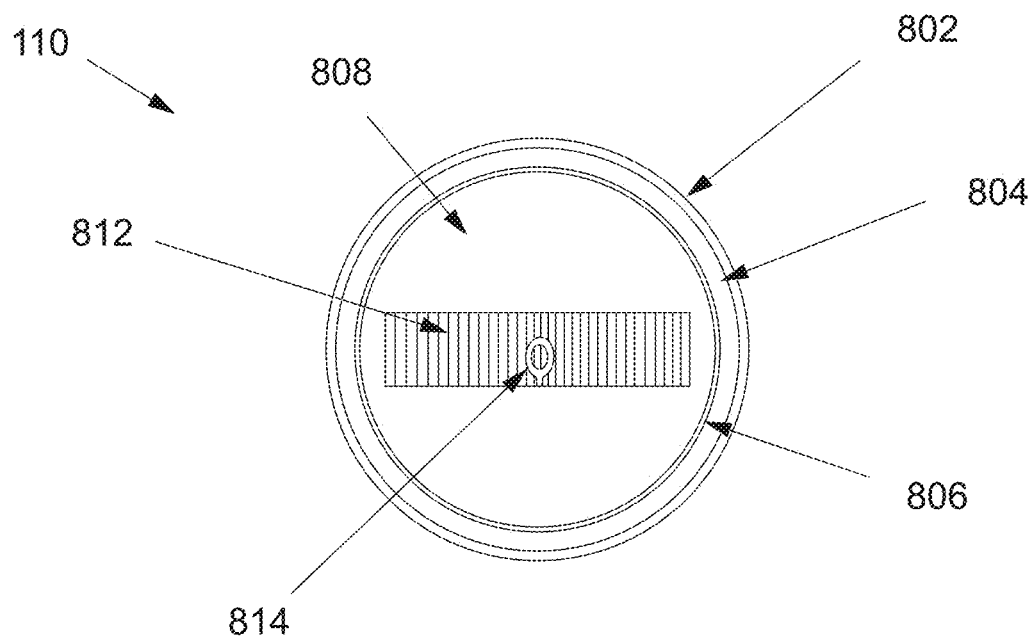
FIG. 8B is a bottom view of the cap assembly of the exemplary erectile dysfunction treatment system in accordance with an alternate embodiment of the invention.

FIG. 8B is a bottom view of the cap assembly of the exemplary erectile dysfunction treatment system in accordance with an alternate embodiment of the invention. In an alternative embodiment of the present invention, the cap assembly consists of an outer shell 802, a gasket 804, a threaded attachment means 806, a cap or lid 808, a spool 812 and a cable centering eyelet 814 for the distraction means. In embodiments of the invention, the outer shell 802 of the cap assembly may be made from a medical-grade polycarbonate resin plastic. However, persons skilled in the art will readily appreciate that alternative embodiments may be made from a number of materials such as, but not limited to, metal and metal alloys, clear acrylic plastics, ABS plastic, HDPE, polycarbonates, polyvinyl chloride (PVC), or various other plastic equivalents. A cap or lid 808 may be a simple extension of the outer shell to form a single unit. In embodiments of the invention, the gasket 804 may be made from materials such as, but not limited to, molded silicone, rubber, latex foam, cork, or various plastics capable of creating an airtight seal for the vacuum cylinder unit. In embodiments of the invention, the threaded attachment means 806 is a female threaded attachment point where the cap end of the frame unit may be inserted and attached. In this view, the spool is positioned to run perpendicular to the frame and distraction means. However, persons skilled in the art will readily appreciate that such a spooling mechanism may run parallel with the frame and distraction means. Persons skilled in the art will readily appreciate that such an attachment may be accomplished through numerous means such as, but not limited to, a threaded screw mechanism or a bayonet mount mechanism. The cap assembly may be molded in such a manner that such attachment means may be part of the cap assembly itself.

The two illustrations of the bottom view of the cap assembly are not meant to be limiting. It will become readily apparent to persons skilled in the art that numerous configurations of the bottom of the cap assembly may be created depending on the distraction means with the cap assembly. For example, and not by limitation, alternative spooling mechanisms which run both parallel and perpendicular to the cap assembly may create different appearances. In embodiments of the invention, an electric motor may be used to turn the screw mechanism or spool and cable mechanism and may create a different appearance. In other embodiments, a ratchet rod and gear and pawl means may be used with one or more rods which may also create a different appearance. In another embodiment, a smooth rod and soft pawl ratcheting means may be used with one or more rods that may also create a different appearance. In another embodiment, a vacuum pump may be used as a distraction means. Persons skilled in the art will readily appreciate that the cap assembly is designed to create a vacuum seal in conjunction with the use of a distraction means.

Figure 9A:
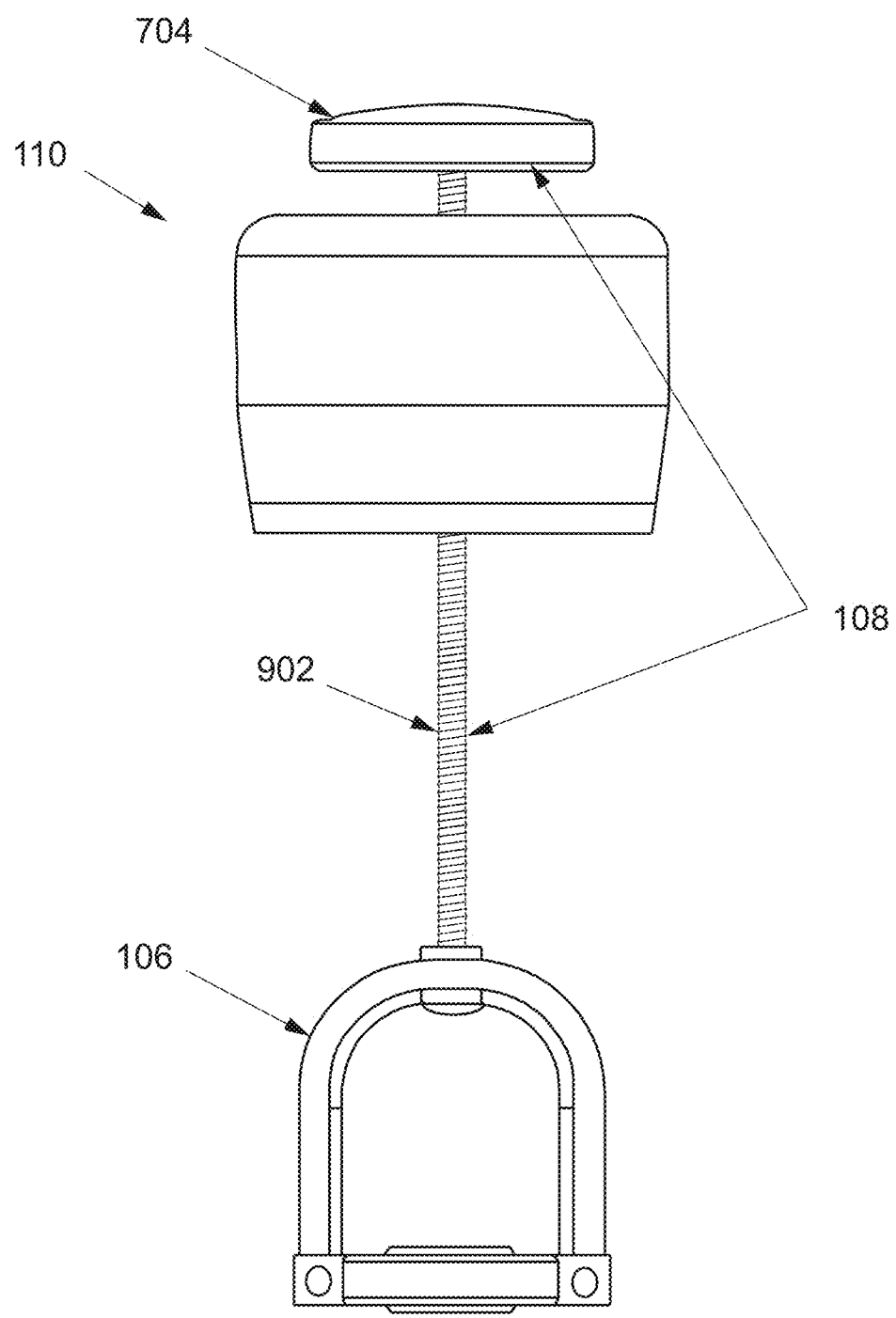
FIG. 9A is a side view of the cap assembly with distraction means and the yoke assembly of the exemplary erectile dysfunction treatment system in accordance with an embodiment of the invention.

FIG. 9A is a side view of the cap assembly with distraction means and the yoke assembly of the exemplary erectile dysfunction treatment system in accordance with an embodiment of the invention. In this view, the distraction means 108 is a simple screw mechanism. A bolt 902 of a given length may simply connect the yoke assembly 106 to the handle 704 of the cap assembly 110. In embodiments of the invention, the length of the bolt is enough so as to move the yoke assembly past the base unit for ease of access. Persons skilled in the art will readily appreciate that there are numerous ways in which to connect a bolt to both the yoke assembly and the handle 704 of the cap assembly 110. In embodiments of the invention, the distraction means 108 can be lengthened, shortened, or otherwise made to apply a greater or lesser amount of distractive force on the penis.

Figure 9B:
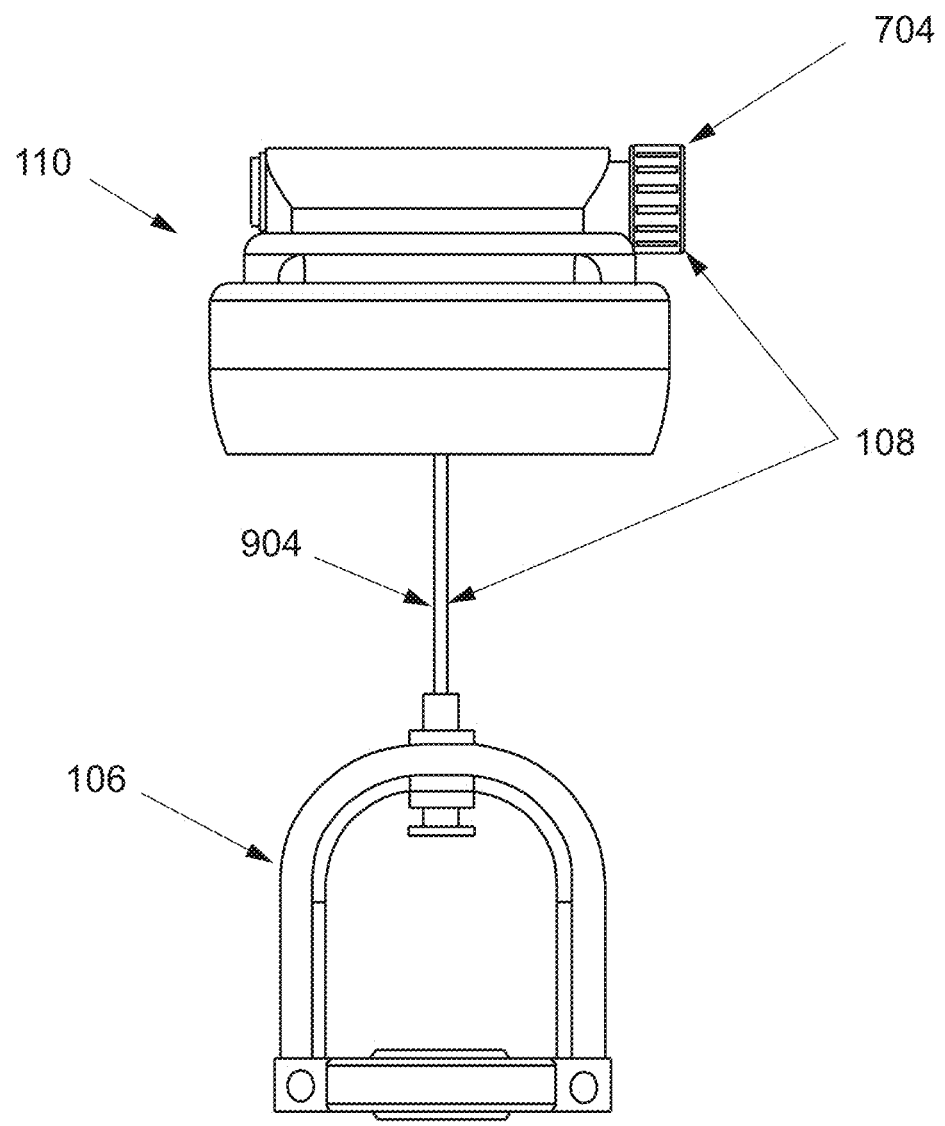
FIG. 9B is a side view of the cap assembly with distraction means and the yoke assembly of the exemplary erectile dysfunction treatment system in accordance with an alternative embodiment of the invention.

FIG. 9B is a side view of the cap assembly with distraction means and the yoke assembly of the exemplary erectile dysfunction treatment system in accordance with an alternative embodiment of the invention. In this view, the distraction means 108 is a cable and spool mechanism. A cable 904 of a given length may simply connect the yoke assembly 106 to the handle 704 of the cap assembly 110. In embodiments of the invention, the length of the cable is enough so as to move the yoke assembly past the base unit for ease of access. Persons skilled in the art will readily appreciate that there are numerous ways in which to connect a cable to both the yoke assembly and the handle 704 of the cap assembly 110. In embodiments of the invention, the distraction means 108 can be lengthened, shortened, or otherwise made to apply a greater or lesser amount of distractive force on the penis.

Figure 10:
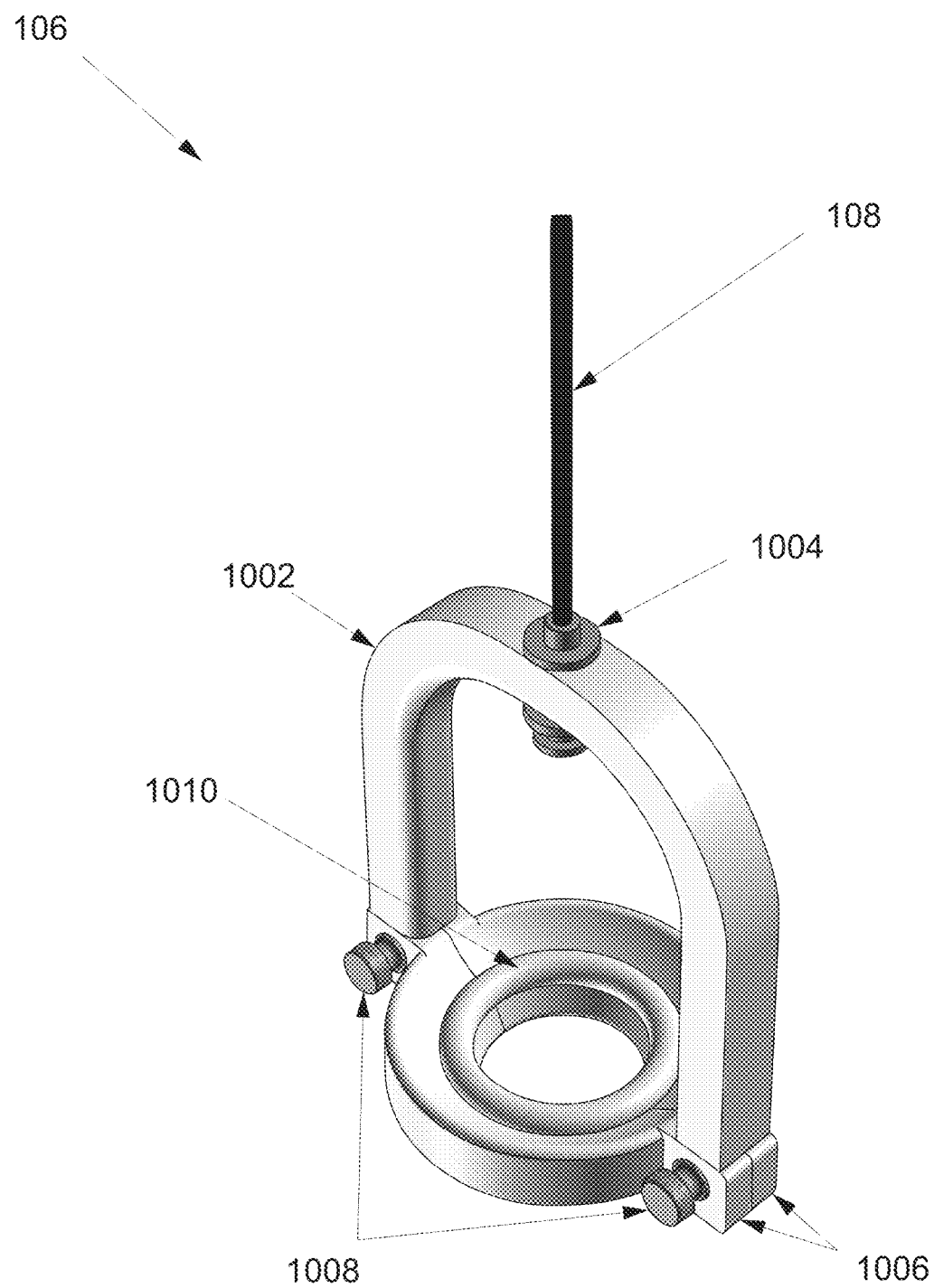
FIG. 10 is a perspective view of the yoke assembly of the exemplary erectile dysfunction treatment system in accordance with an embodiment of the invention.

FIG. 10 is a perspective view of the yoke assembly of the exemplary erectile dysfunction treatment system in accordance with an embodiment of the invention. In this view, the yoke assembly is depicted as being connected to the distraction means 108 wherein the distraction means is depicted as a cable. In other embodiments of the invention, the distraction means 108 may be a bolt. In an embodiment of the invention, the yoke assembly 106 consists of a yoke 1002, a connection means 1004, a clamp assembly 1006, a clamp tightening means 1008 and a clamp ring 1010.

In embodiments of the invention, the yoke 1002 may be U-shaped so as to generally accommodate, secure and support a human penis while undergoing traction and vacuum therapy. On the opposite end of the yoke assembly 1002 from the connection means 1004 is a clamp assembly 1006. The clamp assembly 1006 may consist of two cross-members which may be movably tightenable by a clamp tightening means 1008. The clamp assembly 1006 and clamp tightening means house a clamp ring 1010. Persons skilled in the art will understand that the clamp assembly may attach to the yoke 1002 using numerous means known and appreciated in the art. By way of example, and not limitation, the clamp assembly 1006 may attach to the yoke 1002 through the use of the clamp tightening means 1008 wherein screws may move two cross members closer together or further apart from one another as well as secure the clamp assembly 1006 to the yoke 1002.

The clamp ring 1010 is generally ring-shaped can be made available in various configurations, but is generally designed to fit around the circumference of a human penis. The clamp ring 1010 is also generally designed for a user to insert a penis through the cavity in the clamp ring 1010. For example, in some embodiments of the invention, the clamp ring 1010 can be made available in various degrees of concavity, softness, diameters, and the like. In some embodiments the clamp ring may be custom molded to specifically accommodate a patient's penis depending on need. In other embodiments of the invention, the clamp ring may be shaped in ways to aid in the treatment of Peyronie's disease such as, but not limited to, varying degrees of thickness and varying angles and various configurations used with the clamp assembly. In embodiments of the invention, the clamp ring 1010 may be made from a soft material such as, but not limited to, a foam or a silicone gel capable of softly interfacing with a human penis.

Figure 11A:
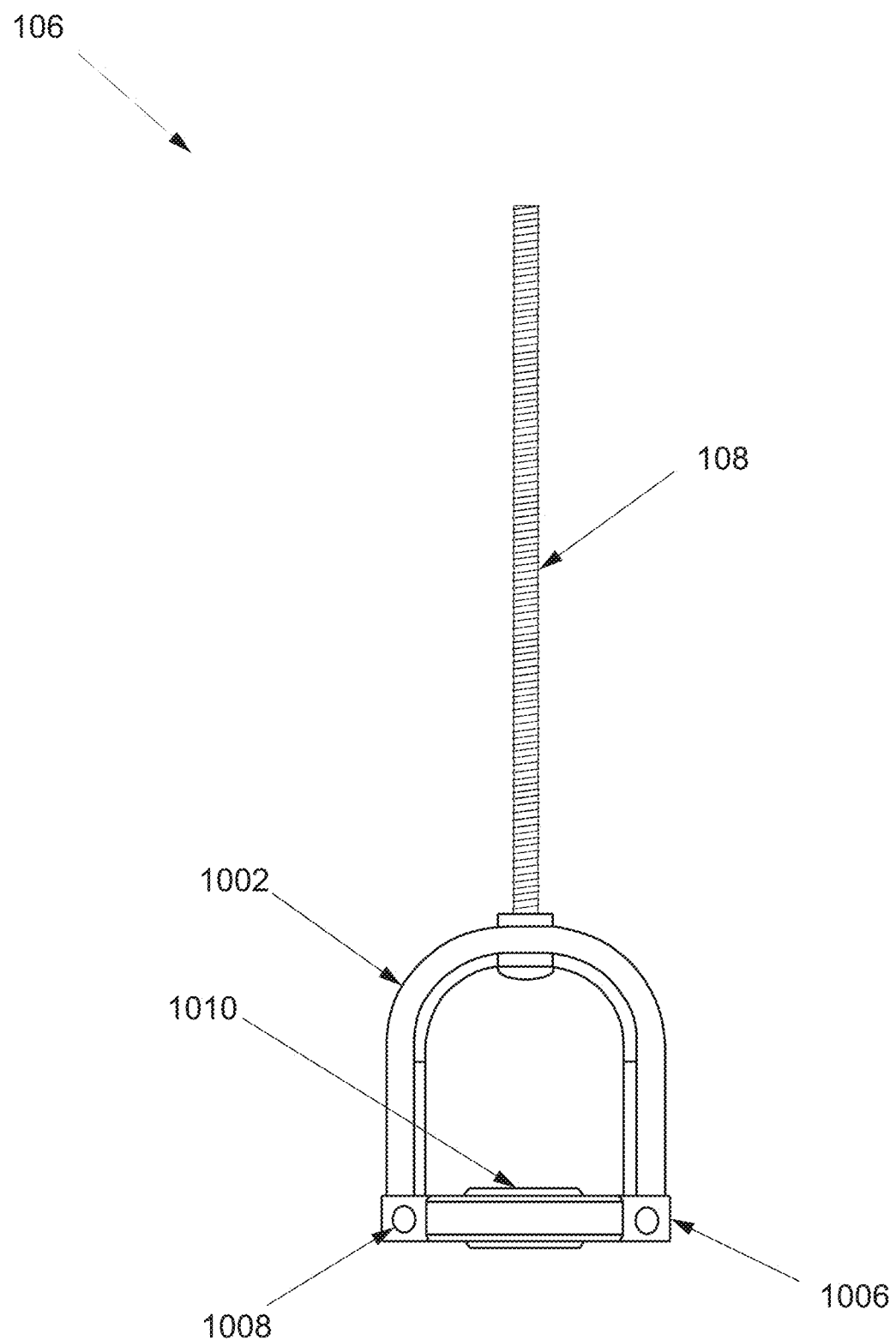
FIG. 11A is a side view of the yoke assembly of the exemplary erectile dysfunction treatment system in accordance with an alternate embodiment of the invention.

FIG. 11A is a side view of the yoke assembly of the exemplary erectile dysfunction treatment system in accordance with an alternate embodiment of the invention. In this view, the yoke assembly is depicted as being connected to the distraction means 108 wherein the distraction means is depicted as a bolt. In other embodiments of the invention, the distraction means 108 may be a cable or other distraction means known and appreciated in the art. In embodiments of the invention the yoke assembly 106 consists of a yoke 1002, a connection means 1004, a clamp assembly 1006, a clamp tightening means 1008 and a clamp ring 1010.

Figure 11B:
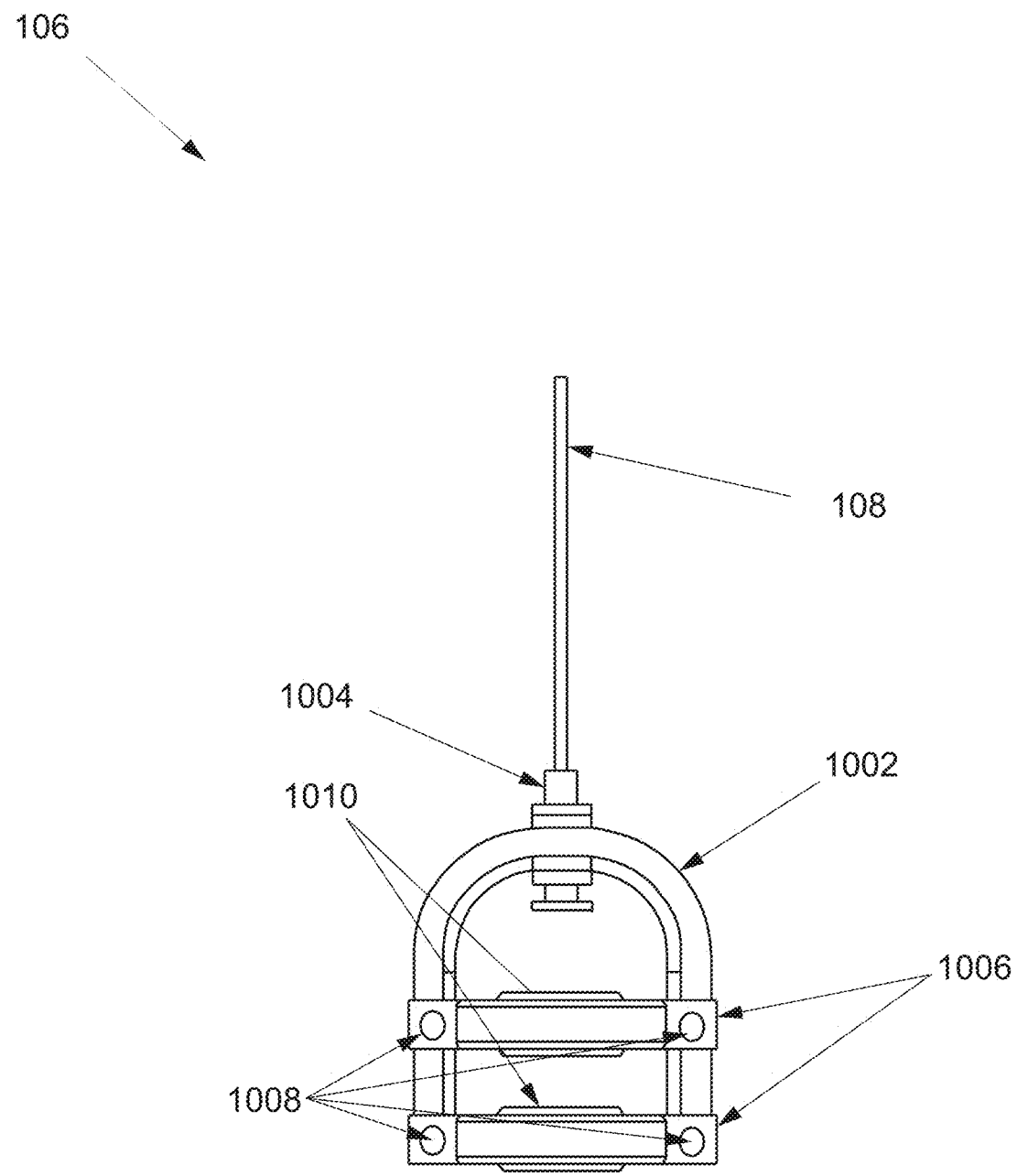
FIG. 11B is a side view of the yoke assembly of the exemplary erectile dysfunction treatment system in accordance with an alternate embodiment of the invention.

FIG. 11B is a side view of the yoke assembly of the exemplary erectile dysfunction treatment system in accordance with an alternate embodiment of the invention. In this view, the yoke assembly is depicted as being connected to the distraction means 108 wherein the distraction means is depicted as a cable. In other embodiments of the invention, the distraction means 108 may be a bolt or other distraction means known and appreciated in the art. The yoke assembly 106 consists of a yoke 1002, a connection means 1004, a clamp assembly 1006, a clamp tightening means 1008 and a clamp ring 1010. In such embodiments, the yoke assembly 106 may include more than one clamp assembly 1006, more than one clamp tightening means 1008 and more than one clamp ring 1010. In other embodiments of the invention, additional clamp assemblies, clamp tightening means and clamp rings may be added to provide additional support and straightening capabilities.

Figure 12:
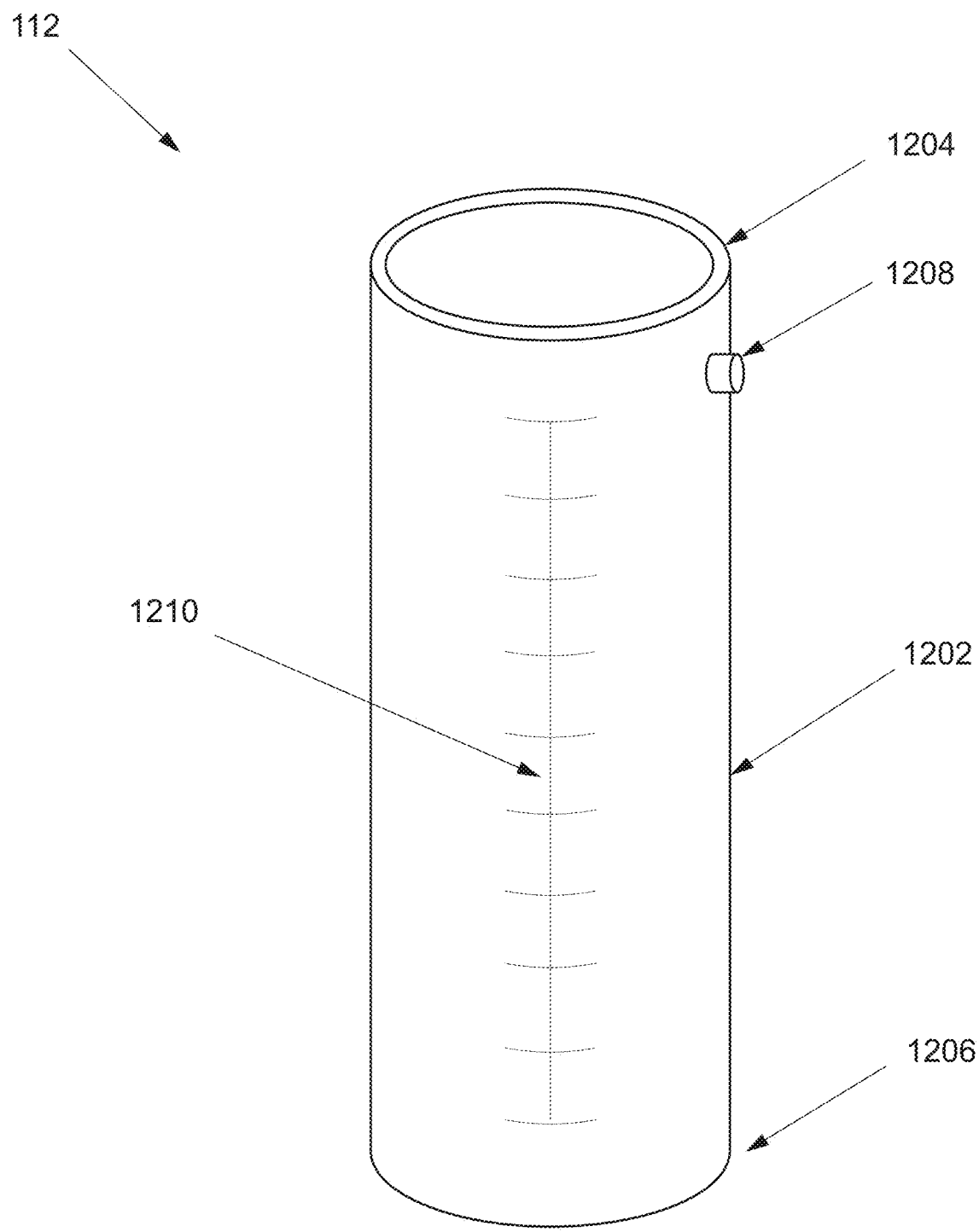
FIG. 12 is a perspective view of the vacuum cylinder unit of the exemplary erectile dysfunction treatment system in accordance with an embodiment of the invention.

FIG. 12 a perspective view of the vacuum cylinder unit 112 of the exemplary erectile dysfunction treatment system in accordance with an embodiment of the invention. The vacuum cylinder unit 112 consists of a body 1202, a proximal end 1204 and a distal end 1206. In this view, the proximal and distal ends of the vacuum cylinder unit 112 have squared ends which engage with the base unit and the gasket of the cap assembly. The length of the vacuum cylinder unit 112 may vary to accommodate differing therapeutic needs of different users of the system. Persons skilled in the art will readily appreciate that other mechanical means for attaching the vacuum cylinder unit 112 to the base unit and the cap assembly include, but are not limited to, a bayonet mount or threaded fittings. At least one vacuum line attachment 1210 may be located at a convenient location along the vacuum cylinder unit 112 and on the sidewall of the body 1202. Visual aids such as graduations 1210 may be located on the outer sidewall of the vacuum cylinder unit. In the preferred embodiment, the vacuum cylinder unit is a plastic body 1202 which may made of a clear, medical-grade polycarbonate resin plastic. However, persons skilled in the art will readily appreciate that alternative embodiments may be made from a number of materials such as, but not limited to, clear acrylic plastics, ABS plastic, polycarbonates, polyvinyl chloride (PVC), or various other plastic equivalents.

Figure 13:
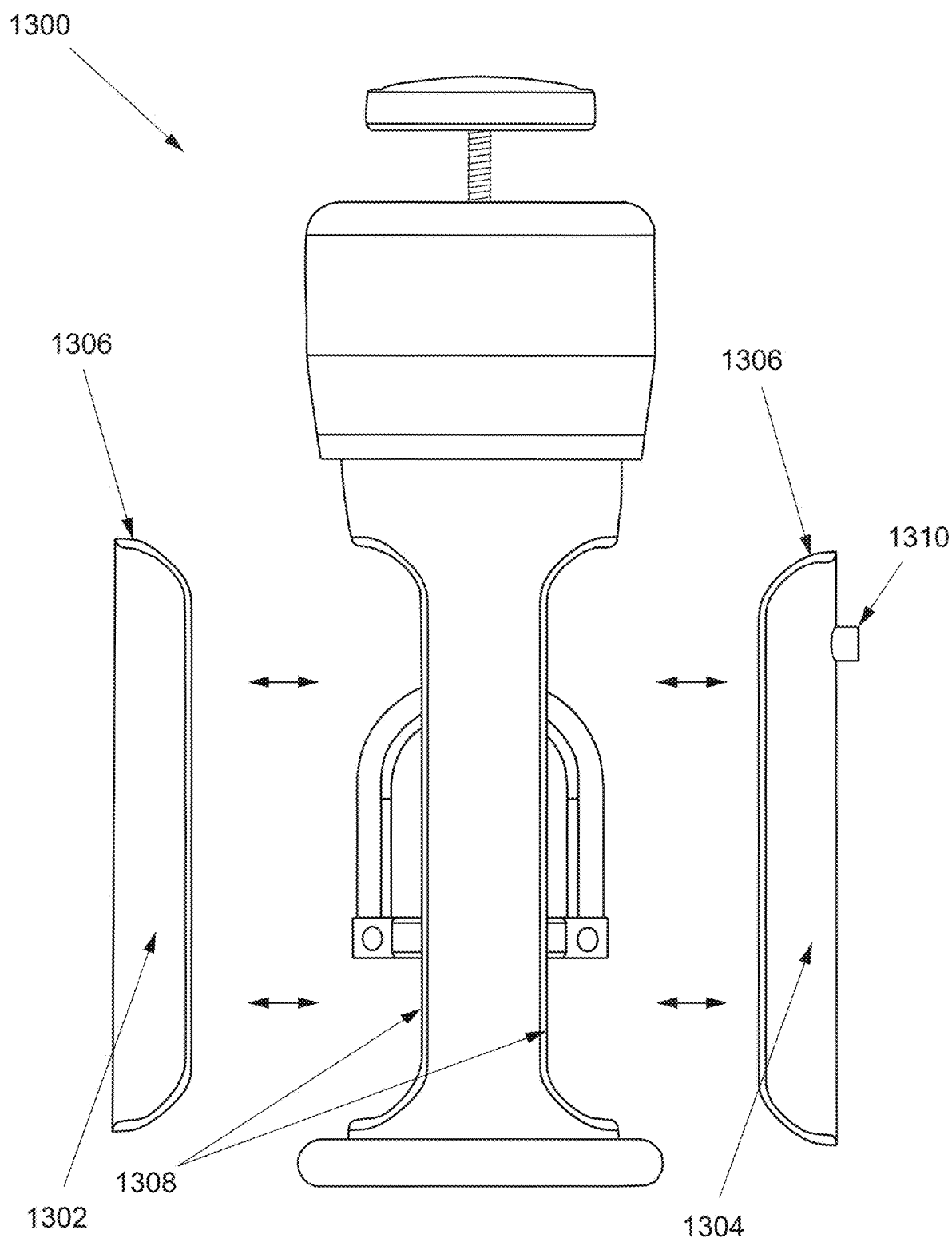
FIG. 13 is a side view of the frame unit and frame seal attachments of the exemplary erectile dysfunction treatment system in accordance with an alternative embodiment of the invention.

FIG. 13 is a side view of the frame unit and frame seal attachments of the exemplary erectile dysfunction treatment system in accordance with an alternative embodiment of the invention. In an alternative embodiment of the invention, two frame seal attachments 1302, 1304 may sealably attach to the cylindrical frame unit. One frame seal attachment 1304 has at least one vacuum line attachment 1310 extending from the sidewall. The frame seal attachments may have beveled edges with a gasket 1306 capable of creating a seal when in contact with the frame unit having beveled edges with a gasket 1308. In such an alternative embodiment of the invention, the frame seal attachments 1302, 1304 simply snap in place when placed in contact with the frame unit. When a vacuum is applied to the frame unit with frame seal attachments 1302, 1304 in place, vacuum therapy may be applied in addition to distraction therapy. Both the frame unit and frame seal attachments may be made from a medical-grade polycarbonate resin plastic and may interface with two vacuum a. However, persons skilled in the art will readily appreciate that alternative embodiments may be made from a number of materials such as, but not limited to, metal and metal alloys, clear acrylic plastics, ABS plastic, polycarbonates, polyvinyl chloride (PVC), or various other plastic equivalents. It will be further understood by persons having skill in the art that numerous materials may be used to create gaskets such as, but not limited to, molded silicone, rubber, latex foam, cork, or various plastics capable of creating an airtight seal when a vacuum is applied. In this view, the frame unit 104 is a cylinder with two openings for a user to access the yoke unit and distraction means as well as to make adjustments to the contents thereof. In various embodiments of the invention, the cap end of the frame unit 402 may be threaded so as to attach to the cap assembly. In other embodiments, the cap end of the frame unit 402 may utilize a different attachment means such as, but not limited to, a bayonet mount or other attachment means known and understood in the art.

Figure 14:
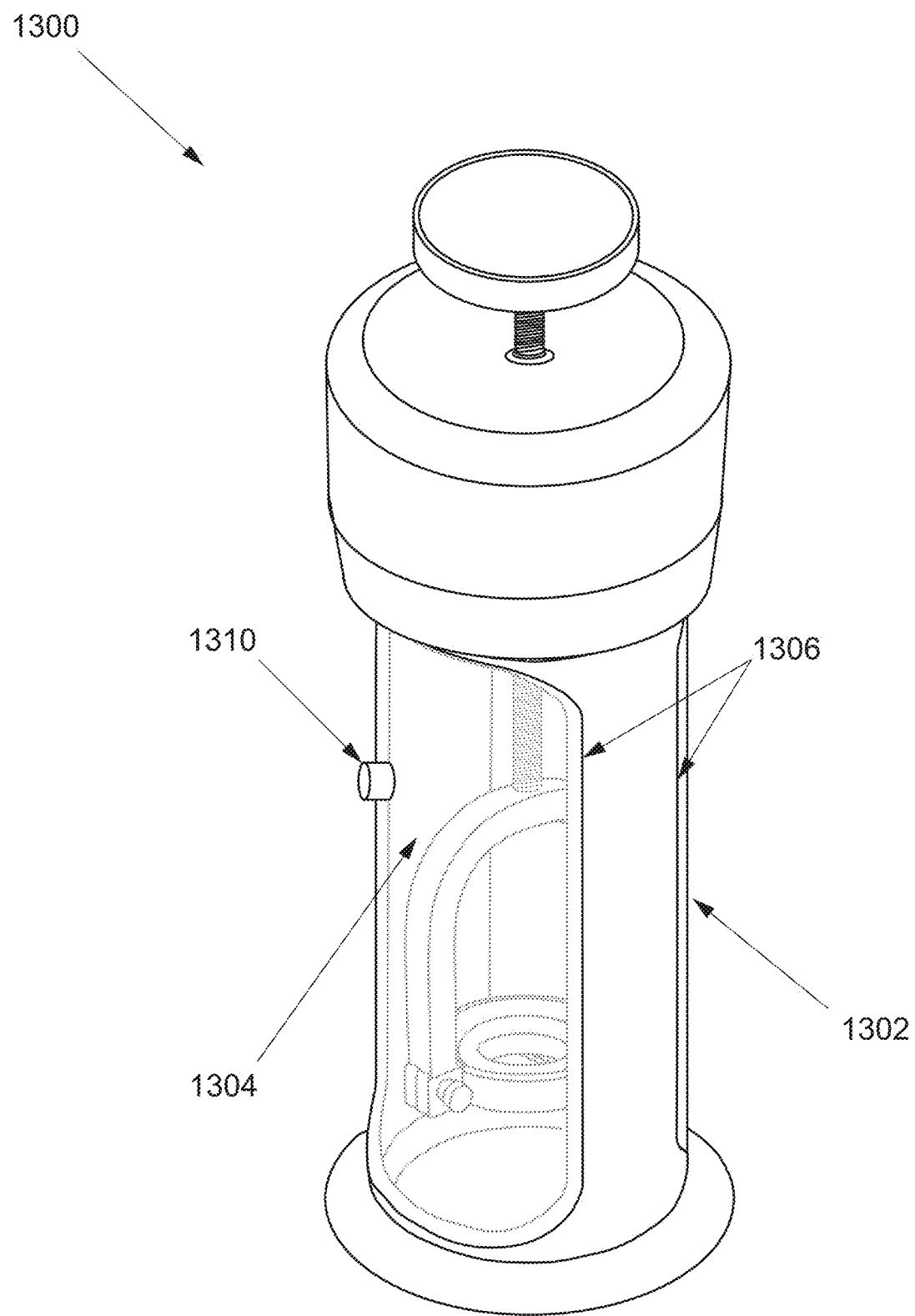
FIG. 14 is a perspective view of the exemplary erectile dysfunction treatment system in accordance with an alternative embodiment of the invention.

FIG. 14 is a perspective view of the exemplary erectile dysfunction treatment system in accordance with an alternative embodiment of the invention. In this view, the two frame seal attachments 1302, 1304 have been attached to the frame unit. Persons skilled in the art will readily appreciate that the two frame seal attachments 1302, 1304 may include beveled edges with gaskets 1306 which will allow the frame seal units to remain in place when inserted into the frame and will provide a seal when a vacuum is ultimately applied to the erectile dysfunction treatment system when in use.

In embodiments of the present invention, a vacuum pump assembly may be detachably affixed to the at least one vacuum line attachment 1310 of the vacuum cylinder unit 112 so that when detached and connected with a length of tubing, the pump assembly may be easily worked with the weighted distal end attached to the main cylinder. The present invention is intended to be used with numerous pumps known in the art and available on the market. This feature provides two operational attributes in one device, both a vacuum device and a traction device.

In the present view, the vacuum line attachments 1310 are depicted as standard vacuum hose attachments where a vacuum pump assembly well known and understood by persons having skill in the art serves as the one-way valve. However, in other embodiments of the invention, various check valves well known in the art may be attached to and extend from the main cylinder. In other embodiments of the invention, a valved male threaded coupling body may be used. Persons skilled in the art will understand that the vacuum line attachments 1310 are designed to incorporate a quick release valve mechanism whether it be incorporated in the pump assembly or in the main cylinder pump attachments.

Use of the erectile dysfunction treatment system is designed to be simple and minimally invasive. Use involves the user or patient preparing the yoke assembly moving the yoke assembly to a point close to the base unit of the invention. The user then prepares and inserts the penis into the yoke assembly by sliding the penis through one or more clamp rings. Preparation of the penis may include, but is not limited to, cleaning and or wrapping the penis in bandages if necessary. The user then secures the penis in the yoke assembly by tightening the clamp assembly through the use of a clamp tightening means. The user may then secure the frame and base unit around the pubic area with the penis secured in the yoke assembly. Optionally, the user may employ a vacuum cylinder or vacuum frame seal attachments to provide contemporaneous vacuum therapy. Once the frame is secured and the vacuum cylinder or frame seal attachments are in place, the user is then able to move the yoke assembly so as to apply a distractive force to the inserted and secured penis. The user may also apply a vacuum to the inserted and secured penis and allowing distractive force and vacuum to operate for a therapeutic amount of time. Upon completion of the therapeutic amount of time, or when the user experiences discomfort, the device may be easily detached by loosening the distraction means and releasing vacuum.

The exemplary erectile dysfunction treatment system may be sold as a single unit or as a kit with interchangeable components. For example, differing base units may be made for differing users with differing needs. In other embodiments, differing cap assemblies with differing distraction means may be sold. In yet other embodiments, vacuum tube assemblies may be sold in lieu of frame seal attachments.

Having fully described at least one embodiment of the exemplary male erectile dysfunction treatment system and method, other equivalent or alternative methods of implementing the male erectile dysfunction treatment system and method according to the present invention will be apparent to those skilled in the art. Various aspects of the invention have been described above by way of illustration, and the specific embodiments disclosed are not intended to limit the invention to the particular forms disclosed. The particular implementation of the male erectile dysfunction treatment system and method may vary depending upon the particular context or application.

By way of example, and not limitation, the erectile dysfunction treatment system and method described in the foregoing patent application is principally directed towards using a standard hand-held vacuum pump. However, similar techniques may instead be applied to fluid-based systems or specialty enlargement systems, which implementations of the present invention are contemplated as within the scope of the present invention. The invention is thus to cover all modifications, equivalents, and alternatives falling within the spirit and scope of the following claims. It is to be further understood that not all of the disclosed embodiments in the foregoing specification will necessarily satisfy or achieve each of the objects, advantages, or improvements described in the foregoing specification.

Although specific features of the invention are shown in some drawings and not others, persons skilled in the art will understand that this is for convenience. Each feature may be combined with any or all of the other features in accordance with the invention. The words "including," "comprising," "having," and "with" as used herein are to be interpreted broadly and comprehensively, and are not limited to any physical interconnection. Claim elements and steps herein may have been numbered and/or lettered solely as an aid in readability and understanding. Any such numbering and lettering in itself is not intended to and should not be taken to indicate the ordering of elements and/or steps in the claims to be added at a later date.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Any amendment presented during the prosecution of the application for this patent is not a disclaimer of any claim element presented in the description or claims to be filed. Persons skilled in the art cannot reasonably be expected to draft a claim that would literally encompass each and every equivalent.

What is claimed is:

1. An erectile dysfunction treatment system comprising:
   a base unit capable of interfacing with a human body;
   a cylindrical frame unit with two open sides, said cylindrical frame unit with two open sides having beveled edges and a gasket mechanism wherein a vacuum cylinder assembly is created with two frame seal attachments with at least one vacuum line attachment sealingly attached to at least one frame seal attachment creating a sealed cylinder;
   a yoke assembly capable of interfacing with a human penis; and
   a cap assembly with a built-in distraction mechanism for moving the said yoke assembly capable of interfacing with a human penis and applying a distractive force on a human penis.

2. The erectile dysfunction treatment system of claim 1 wherein the base capable of interfacing with the human body attaches to the cylindrical frame unit and serves to form a seal between the erectile dysfunction treatment system and a human body.

3. The erectile dysfunction treatment system of claim 1 wherein the cap assembly with a built-in distraction mechanism for moving the said yoke assembly capable of interfacing with a human penis and applying a distractive force on a human penis attaches to the to the cylindrical frame unit on the end opposite of the base unit.

4. The erectile dysfunction treatment system of claim 1 wherein the cap assembly with a built-in distraction mechanism for moving the said yoke assembly capable of interfacing with a human penis and applying a distractive force on a human penis is sealingly attachable to the frame unit with a gasket means capable of creating an airtight seal.

5. The erectile dysfunction treatment system of claim 1 wherein a vacuum cylinder assembly consisting of a vacuum cylinder and at least one vacuum line attachment is slidable over the cylindrical frame unit wherein one end of the said vacuum cylinder assembly forms a seal with the base unit and the other end of the vacuum cylinder assembly forms a seal with a gasket housed in the cap assembly.

6. The erectile dysfunction treatment system of claim 1 wherein the yoke assembly capable of interfacing with a human penis consists of a generally u-shaped yoke, a connection means, a clamp assembly, a clamp tightening means and a clamp ring.

7. The erectile dysfunction treatment system of claim 6 wherein the clamp ring of the yoke assembly is designed to fit around the circumference of a human penis and secure a human penis with the said clamp assembly and the said clamp tightening means.

8. The erectile dysfunction treatment system of claim 1 wherein the yoke assembly is movably connectable to the cap assembly with distraction means and attaches to the said distraction means.

9. The erectile dysfunction treatment system of claim 8 wherein the cap assembly with a built-in distraction mechanism for moving the said yoke assembly capable of interfacing with a human penis and applying a distractive force on a human penis consists of a screw mechanism which can move the yoke assembly so as to apply distractive force when a penis is inserted and secured in the said yoke assembly.

10. An erectile dysfunction treatment system comprising:
    a base unit capable of interfacing with a human body;
    a cylindrical frame unit with two open sides, said cylindrical frame unit with two open sides having beveled edges and a gasket mechanism wherein a vacuum cylinder assembly is created with two frame seal attachments with at least one vacuum line attachment sealingly attached to the frame unit creating a sealed cylinder;
    a vacuum cylinder assembly;
    at least one vacuum line attachment;
    a yoke assembly capable of interfacing with a human penis; and
    a cap assembly with a built-in distraction mechanism for moving the said yoke assembly capable of interfacing with a human penis and applying a distractive force on a human penis.

11. The erectile dysfunction treatment system of claim 1 wherein the base capable of interfacing with the human body attaches to the cylindrical frame unit and serves to form a seal between the erectile dysfunction treatment system and a human body.

12. The erectile dysfunction treatment system of claim 10 wherein the cap assembly with a built in distraction mechanism attaches to the to the frame on the end opposite of the base unit.

13. The erectile dysfunction treatment system of claim 10 wherein a wherein a vacuum cylinder assembly consisting of a vacuum cylinder and at least one vacuum line attachment is slidable over the frame unit wherein one end of the said vacuum cylinder assembly forms a seal with the base unit and the other end of the vacuum cylinder assembly forms a seal with a gasket housed in the cap assembly.

14. The erectile dysfunction treatment system of claim 1 wherein the yoke assembly capable of interfacing with a human penis consists of a generally u-shaped yoke, a connection means, a clamp assembly, a clamp tightening means and a clamp ring.

15. The erectile dysfunction treatment system of claim 14 wherein the clamp ring of the yoke assembly is configured to fit around the circumference of a human penis and secure a human penis with the said clamp assembly and the said clamp tightening means.

16. The erectile dysfunction treatment system of claim 1 wherein the yoke assembly is movably connectable to the cap assembly with distraction mechanism and attaches to the said distraction means.

17. The erectile dysfunction treatment system of claim 16 wherein the cap assembly with a built-in distraction means for moving the said yoke assembly capable of interfacing with a human penis and applying a distractive force on a human penis consists of a screw mechanism which can move the yoke assembly so as to apply distractive force when a penis is inserted and secured in the said yoke assembly.

18. A method of treating erectile dysfunction using an erectile treatment system comprising a base unit capable of interfacing with a human body; a cylindrical frame unit with two open sides, said cylindrical frame unit with two open sides having beveled edges and a gasket mechanism wherein a vacuum cylinder assembly is created with two frame seal attachments with at least one vacuum line attachment sealingly attached to the frame unit creating a sealed cylinder; a yoke assembly capable of interfacing with a human penis consisting of a generally u-shaped yoke, a connection means, a clamp assembly, a clamp tightening means and a clamp ring; and a cap assembly with a built-in distraction mechanism; said method comprising the steps of:
- a. preparing the said yoke assembly;
- b. preparing the penis for insertion into the said yoke assembly;
- c. inserting penis into the clamp ring of the said yoke assembly;
- d. securing the penis inserted into clamp ring in the yoke assembly;
- e. creating a vacuum cylinder assembly around the frame unit with the penis inserted to the yoke assembly;
- f. moving the yoke assembly so as to apply a distractive force to the inserted and secured penis;
- g. applying vacuum to the said vacuum cylinder; and
- h. allowing distractive force and vacuum to operate for a therapeutic amount of time.

* * * * *